(12) United States Patent
Stern et al.

(10) Patent No.: US 8,298,992 B2
(45) Date of Patent: Oct. 30, 2012

(54) LOW ODOR, LOW VOLATILITY SOLVENT FOR AGRICULTURAL CHEMICALS

(75) Inventors: Alan J. Stern, Magnolia, TX (US);
David Ferguson, Spring, TX (US);
Howard Stridde, George West, TX (US)

(73) Assignee: Huntsman Petrochemical LLC, The Woodlands, TX (US)

( * ) Notice: Subject to any disclaimer, the term of this patent is extended or adjusted under 35 U.S.C. 154(b) by 743 days.

(21) Appl. No.: 12/300,482

(22) PCT Filed: May 25, 2007

(86) PCT No.: PCT/US2007/069793
§ 371 (c)(1),
(2), (4) Date: Nov. 12, 2008

(87) PCT Pub. No.: WO2007/140332
PCT Pub. Date: Dec. 6, 2007

(65) Prior Publication Data
US 2009/0181850 A1   Jul. 16, 2009

Related U.S. Application Data

(60) Provisional application No. 60/809,100, filed on May 26, 2006.

(51) Int. Cl.
*A01N 43/40* (2006.01)
*A01N 43/44* (2006.01)
*A01N 43/36* (2006.01)

(52) U.S. Cl. ....... 504/130; 514/65; 514/237.5; 514/317; 514/423

(58) Field of Classification Search ............... 504/320, 504/130; 544/106; 546/184; 548/500; 514/65, 514/237.5, 317, 423
See application file for complete search history.

(56) References Cited

U.S. PATENT DOCUMENTS

| | | | | |
|---|---|---|---|---|
| 2,778,826 A | * | 1/1957 | Schmidle | 546/192 |
| 3,074,940 A | * | 1/1963 | Benzing | 544/178 |
| 3,342,673 A | * | 9/1967 | Kaufman et al. | 514/443 |
| 5,283,229 A | | 2/1994 | Narayanan et al. | |
| 2005/0137091 A1 | | 6/2005 | Herold et al. | |
| 2005/0215433 A1 | | 9/2005 | Benitez et al. | |

OTHER PUBLICATIONS

Masuyama A., Preparation and Surface Active Properties of Terminal Amide Type of Alcohol Ethoxylates, Jun. 1989, JAOCS, vol. 66, No. 6, pp. 834-837.*

* cited by examiner

*Primary Examiner* — Brian-Yong S Kwon
*Assistant Examiner* — Andriae M Holt
(74) *Attorney, Agent, or Firm* — Huntsman International LLC

(57) ABSTRACT

A composition includes an agricultural component in an amount of at least about 27% by weight and a solvent composition in an amount not greater than about 55% by weight. The solvent composition includes an amide having a structure of Formula I:

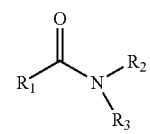

(I)

wherein $R_1$ comprises a $C_3$ to $C_{15}$ hydrocarbon group, and wherein $R_2$ and $R_3$ comprise a $C_1$ or higher hydrocarbon group.

18 Claims, No Drawings

LOW ODOR, LOW VOLATILITY SOLVENT FOR AGRICULTURAL CHEMICALS

CROSS-REFERENCE TO RELATED APPLICATION(S)

This application is the National Phase Of International Application PCT/US2007/069793 filed May 25, 2007 which designated the U.S. and claims priority to U.S. Utility Provisional Patent Application No. 60/809,100, filed May 26, 2006, entitled "LOW ODOR, LOW VOLATILITY SOLVENT FOR AGRICULTURAL CHEMICALS," naming inventors Alan J. Stern, Dave Ferguson, and Howard Stridde, which application is incorporated by reference herein in its entirety.

TECHNICAL FIELD

This invention, in general, relates to solvents, and more particularly to the field of organic solvents for pesticides.

BACKGROUND

Solvents have typically been used in a preparation of agricultural chemical formulations. For example, organic solvents were frequently used in various formulation types since at least the 1950's when pesticide products were first developed and used on a large scale. However, many common solvents exhibit either high water solubility or poor solvency of agricultural chemicals.

Those typical solvents that exhibit high water solubility provide an environmental risk when used in large quantities, such as in agriculture. For example, such water soluble solvents may enter the water system, such as rivers, lakes, and aquifers, contaminating water supplies.

On the other hand, those traditional solvents that have low water solubility may also exhibit poor solvent characteristics with respect to particular agricultural chemicals. As such, a low ratio of agricultural chemicals to solvent is used, resulting in a large quantity of solvent being used to deliver a small quantity of an agricultural chemical.

Consequently, an improved organic solvent would be desirable.

SUMMARY OF THE INVENTION

In a particular embodiment, a composition includes an NTF pesticide and a solvent composition in an amount not greater than about 55% by weight. The solvent composition includes an amide having a structure of

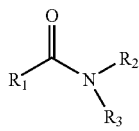

wherein $R_1$ comprises a $C_3$ to $C_{15}$ hydrocarbon group, and wherein $R_2$ and $R_3$ comprise a $C_1$ or higher hydrocarbon group.

In another exemplary embodiment, a composition includes an agricultural component in an amount of at least about 27% by weight and a solvent composition in an amount not greater than about 55% by weight. The solvent composition includes an amide having a structure of

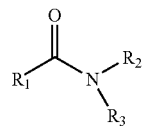

wherein $R_1$ comprises a $C_3$ to $C_{15}$ hydrocarbon group, and wherein $R_2$ and $R_3$ comprise a $C_1$ or higher hydrocarbon group.

In a further exemplary embodiment, a composition includes an agricultural component and a morpholine amide in an amount not greater than about 55% by weight of the composition. The ratio of the amount of agricultural component to the amount of morpholine amide is at least about 0.8.

In another exemplary embodiment, a composition includes an herbicidal component and a solvent composition including a morpholine amide component.

In an additional embodiment, a composition includes an insecticidal component and a solvent composition including a morpholine amide component.

In another exemplary embodiment, a method of preparing an agricultural composition includes blending an amide solvent in an amount not greater than about 55% by weight with an agricultural component in an amount of at least about 27% by weight to form a solution and blending an emulsifier with the solution. The amide solvent has a structure of

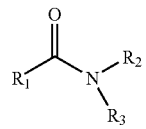

wherein $R_1$ comprises a $C_3$ to $C_{15}$ hydrocarbon group, and where at $R_2$ and $R_3$ comprise a $C_1$ or higher hydrocarbon group.

DESCRIPTION OF THE PREFERRED EMBODIMENT(S)

In a particular embodiment, an agricultural composition includes an agricultural component and a solvent composition. For example, the agricultural component may be a pesticide, such as an herbicide, plant growth regulator, an insecticide, or insect growth regulator. The solvent composition may include one or more solvents and, in particular, may include an amide solvent. For example, the amide solvent may be derived from a carboxylic acid (e.g., $C_4$-$C_{16}$ fatty acid) combined with an amine. In particular, the fatty acid amide may include a morpholine fatty acid amide.

The composition may take the form of an emulsifiable concentrate, water based emulsion, suspo-emulsion, or micro-emulsifiable concentrate. In particular, the agricultural composition may include an agricultural component, a solvent composition, and an emulsifier or emulsifier blend. In addition, the agricultural composition may include a second agricultural component in the form of a liquid or solid.

The agricultural component may be a pesticide. In an exemplary embodiment, the pesticide includes a fungicide, a bactericide, an herbicide, a plant growth regulator, an insecticide, or an insect growth regulator. In an example, the fungicide may include an aliphatic nitrogen fungicide, an amide fungicide, an antibiotic fungicide, an aromatic fungicide, a benzimidazole fungicide, a benzimidazole precursor fungicide, a benzothiazole fungicide, a bridged diphenyl fungicide, a carbamate fungicide, a conazole fungicide, a dicarboximide fungicide, a dinitrophenol fungicide, dithiocarbamate fungicide, an imidazole fungicide, a morpholine fungicide, an organophosphate fungicide, an oxathiin fungicide, an oxazole fungicide, a pyridine fungicide, a pyrimidine fungicide, a pyrrole fungicide, a quinoline fungicide, a quinone fungicide, a quinioxaline fungicide, a thiazole fungicide, a thiocarbamate fungicide, a thiophene fungicide, a triazine fungicide, a triazole fungicide, a urea fungicide, or another fungicide, or any combination thereof.

In an example, the aliphatic nitrogen fungicide may include butylamine; cymoxanil; dodicin; dodine; guazatine; iminoctadine; or any combination thereof. In a further example, an amide fungicide may include carpropamid; chloraniformethan; cyazofamid; cyflufenamid; diclocymet; ethaboxam; fenoxanil; flumetover; furametpyr; prochloraz; quinazamid; silthiofam; triforine; benalaxyl; benalaxyl-M; furalaxyl; metalaxyl; metalaxyl-M; pefurazoate; benzohydroxamic acid; tioxymid; thrichlamide; zarilamid; zoxamide; cyclaburamid; furmecyclox dichlofluanid; tolylfluanid; benthiavalicarb; iprovalicarb; benalaxyl; benalaxyl-M; boscalid; carboxin; fenhexamid; metsulfovax; ofurace; oxadixyl; oxycarboxin; pyracarbolid; thifluzamide; tiadinil; benodanil; flutolanil; mebenil; melpronil; salicylanilide; tecloftalam fenfuram; furalaxyl; furcarbanil; methfuroxam; flusulfamide; or any combination thereof.

In a further example, an antibiotic fungicide may include aureofungin; blasticidin-S; cycloheximide; griseofulvin; kasugamycin; natamycin; polyoxins; polyoxorim; streptomycin; validamycin; azoxystrobin; dimoxystrobin; fluoxastrobin; kresoxim-methy; metominostrobin; orysastrobin; picoxystrobin; pyraclostrobin; trifloxystrobin; or any combination thereof. In another exemplary embodiment, an aromatic fungicide may include biphenyl; chlorodinitronaphthalene; chloroneb; chlorothalonil; cresol; dicloran; hexachlorobenzene; pentachlorophenol; quintozene; sodium pentachlorophenoxide; tecnazene; or any combination thereof. In an additional example, a benzimidazole fungicide may include benomyl; carbendazim; chlorfenazole; cypendazole; debacarb; fuberidazole; mecarbinzid; rabenzazole; thiabendazole; or any combination thereof. In another example, a benzimidazole precursor fungicide may include furophanate; thiophanate; thiophanate-methyl; or any combination thereof.

In an additional example, a benzothiazole fungicide may include bentaluron; chlobenthiazone; TCMTB; or any combination thereof. In another example, a bridged diphenyl fungicide may include bithionol; dichlorophen; diphenylamine; or any combination thereof. In a further example, a carbamate fungicide may include benthiavalicarb; furophanate; iprovalicarb; propamocarb; thiophanate; thiophanate-methyl; benomyl; carbendazim; cypendazole; debacarb; mecarbinzid; diethofencarb, iodopropynyl butylcarbamate; or any combination thereof. In a further example, a conazole fungicide may include climbazole; clotrimazole; imazalil; oxpoconazole; prochloraz; triflumizole; azaconazole; bromuconazole; cyproconazole; diclobutrazol; difenoconazole; diniconazole; diniconazole-M; epoxiconazole; etaconazole; fenbuconazole; fluquinconazole; flusilazole; flutriafol; furconazole; furconazole-cis hexaconazole; imibenconazole; ipconazole; metconazole; myclobutanil; penconazole; propiconazole; prothioconazole; quinconazole; simeconazole; tebuconazole; tetraconazole; triadimefon; triadimenol; triticonazole; uniconazole; uniconazole-P; or any combination thereof.

In another example, a dicarboximide fungicide may include famoxadone; fluoroimide; chlozolinate; dichlozoline; iprodione; isovaledione; myclozolin; procymidone; vinclozolin; captafol; captan; ditalimfos; folpet; thiochlorfenphim; or any combination thereof. In a further example, a dinitrophenol fungicide may include binapacryl; dinobuton; dinocap; dinocap-4; dinocap-6; dinocton; dinopenton; dinosulfon; dinoterbon; DNOC; or any combination thereof. In an additional example, a dithiocarbamate fungicide may include azithiram; carbamorph; cufraneb; cuprobam; disulfiram; ferbam; metam; nabam; tecoram; thiram; ziram; dazomet; etem; milneb; mancopper; mancozeb; maneb; metiram; polycarbamate; propineb; zineb; or any combination thereof.

In an additional example, an imidazole fungicide may include cyazofanid; fenamidone; fenapanil; glyodin; iprodione; isovaledione; pefurazoate; trazoxide; or any combination thereof. In another example, a morpholine fungicide may include aldimorph; benzamorph; carbamorph; dimethomorph; dodemorph; fenpropimorph; flumorph; tridemorph; or any combination thereof.

In another example, an organophosphate fungicide may include ampropylfos; ditalimfos; edifenphos; fosetyl; hexylthiofos; iprobenfos; phosdiphen; pyrazophos; tolclofos-methyl; triamiphos; or any combination thereof. In a further example, an oxathliin fungicide may include carboxin; oxycarboxin; or any combination thereof. In an additional example, an oxazole fungicide may include chlozolinate; dichlozoline; drazoxolon; famoxadone; hymexazol; metazoxolon; myclozolin; oxadixyl; vinclozalin; or any combination thereof. In an additional example, a pyridine fungicide may include boscalid; buthiobate; dipyrithione; fluazinam; pyridinitril; pyrifenox; pyroxychlor; pyroxyfur; or any combination thereof.

In a further example, a pyrimidine fungicide may include bupirimate; cyprodinil, diflumetorim; dimethirimol; ethirimol; fenarimol; ferimzone; mepanipyrim; nuarimol; pyrimethanil; triarimol; or any combination thereof. In an additional example, a pyrrole fungicide may include fenpiclonil; fludioxonil; fluoroimide; or any combination thereof. In another example, a quinoline fungicide may include ethoxyquin; halacrinate, 8-hydroxyquinoline sulfate; quinacetol; quinoxyfen; or any combination thereof. In a further example, a quinone fungicide may include benquinox; chloranil; dichlone; dithianon; or any combination thereof.

In another example, a quinoxaline fungicide may include chinomethionat; chlorquinox; thioquinox; or any combination thereof. In a further example, a thiazole fungicide may include ethaboxam; etridiazole; metsulfovax; octhilinone; thiabendazole; thiadifluor; thifluzamide; or any combination thereof. In an additional example, a thiocarbamate fungicides may include methasulfocarb; prothiocarb; or any combination thereof. In a further example, a thiophene fungicide may include ethaboxam; silthiofam; or any combination thereof. In a further example, a triazine fungicide may include anilazine. In another example, a triazole fungicide may include bitertanol; fluotrimazole; triazbutil; or any combination thereof. In an additional example, a urea fungicide may include bentaluron; pencycuron; quinazamid; or any combination thereof. Another fungicide may include acibenzolar; acypetacs; allyl alcohol benzalkonium chloride; benzamacril; bethoxazin; carvone; chloropicrin; DBCP; dehydroacetic acid diclomezine; diethyl pyrocarbonate; fenaminosulf; fenitropan; fenpropidin; formaldehyde furfural; hexachlorobutadiene; iodomethane; isoprothiolane; methyl bromide; methyl isothiocyanate; metrafenone; nitrostyrene; nitrothal-isopropyl OCH; 2 phenylphenol phthalide; piperalin; probenazole; proquinazid; pyroquilon; sodium orthophenylphenoxide;

spiroxamine; sultropen; thicyofen; tricyclazole; chitin; chitosan; 4-cumylphenol; 4-alpha-cumylphenol; or any combination thereof.

In an example, the fungicide may be a non-triazole functional (NTF) fungicide, including a fungicide other than a triazole fungicide and triazole-functional conazole fungicides. Non-triazole functional compounds excludes those compounds that include a triazole group. Furthermore, the pesticide may be an NTF pesticide, including NTF fungicide, NTF bactericide, NTF herbicide, NTF plant growth regulator, NTF insecticide, NTF insect growth regulator, or any combination thereof. In particular, the inventors have discovered that particular solvent compositions exhibit advantageous solvent properties for particular NTF pesticides and particular classes of NTF pesticides.

For example, the herbicide may be an amide or anilide type herbicide, a phenoxy type herbicide, a sulfonylurea type herbicide, an aryloxyalkanoic acid type herbicide, a cyclohexanedione oxime type herbicide, urethane type herbicides, isoxazolidinone type herbicide, pyridinyloxy acetic acid type herbicide, or any combination thereof. In a particular embodiment, the herbicide is an amide type herbicide or an anilide type herbicide, such as propanil. In another exemplary embodiment, the herbicide is a phenoxy type herbicide, such as 2,4-dichlorophenoxy acetic acid (2,4-D acid). In a further example, the composition may include a sulfonylurea type herbicide, such as chlolosulfuron. In an additional example, the herbicide may include an aryloxyalklanoic acid type herbicide. In another example, the herbicide may include a cyclohexanedione oxime type herbicide. In a further example, the herbicide may include a urethane type herbicide, such as phenmediphan or desmediphan. In another example, the herbicide may include an isoxazolidinone type herbicide, such as clomazone. In an additional example, the herbicide may include a pyridinyloxy acetic acid type herbicide, such as triclopyr. Further, the herbicide may be selected from an herbicide of the classes and subclasses listed below.

In an example, an amide type herbicide may include allidochlor; beflubutamid; benzadox; benzipram; bromobutide; cafenstrole; CDEA; cyprazole; dimethenamid; dimethenamid-P; diphenamid; epronaz; etnipromid; fentrazamide; flupoxam; fomesafen; halosafen; isocarbamid; isoxaben; napropamide; naptalam; pethoxamid; propyzamide; quinonamid; tebutam; or any combination thereof.

In a further example, an anilide herbicide may include chloranocryl; cisanilide; clomeprop; cypromid; diflufenican; etobenzanid; fenasulam; flufenacet; flufenican; mefenacet; mefluidide; metamifop; monalide; naproanilide; pentanochlor; picolinafen; propanil; or any combination thereof.

In an additional example, an arylalanine herbicide may include benzoylprop; flamprop; flamprop-M; or any combination thereof.

In another example, a chloroacetanilide herbicide may include acetochlor; alachlor; butachlor; butenachlor; delachlor; diethatyl; dimethachlor; metazachlor; metolachlor; S-metolachlor; pretilachlor; propachlor; propisochlor; prynachlor; terbuchlor; thenylchlor; xylachlor; or any combination thereof.

In an example, a sulfonanilide herbicide may include benzofluor; cloransulam; diclostulam; florasulam; flumetsulam; metosulam; perfluidone; pyrimisulfan; profluazol; or any combination thereof.

In another example, a sulfonamide herbicide may include asulam; carbasulam; fenasulam; oryzalin; penoxsulam; pyroxsulam; or any combination thereof.

In a further example, a thioamide herbicide may include bencarbazone; chlorthiamid; or any combination thereof.

In an additional example, an antibiotic herbicide may include bilanafos. Other herbicides include aromatic acid herbicides.

In another example, a benzoic acid herbicide may include chloramben; dicamba; 2,3,6-TBA; tricamba; or any combination thereof.

In an additional example, a pyrimidinyloxybenzoic acid herbicide may include bispyribac; pyriminobac; or any combination thereof. Further, a pyrimidinylthiiobenzoic acid herbicide may include pyrithiobac.

In a further example, a phthalic acid herbicide may include chlorthal. In addition, a picolinic acid herbicide may include aminopyralid; clopyralid; picloram; or any combination thereof.

In another example, a quinolinecarboxylic acid herbicide may include quinclorac; quinmerac; or any combination thereof. An arsenical herbicide may include cacodylic acid; CMA; DSMA; hexaflurate; MAA; MAMA; MSMA; potassium arsenite; sodium arsenite; or any combination thereof.

In a further example, a benzoylcyclolhexanedione herbicide may include mesotrione; sulcotrione; tefuryltrione; tembotrione; or any combination thereof. A benzofuranyl alkylsulfonate herbicide may include benfuresate; ethofumesate; or any combination thereof.

Further, a carbamate herbicide may include asulam; carboxazole; chlorprocarb; dichlormate; fenasulam; karbutilate; terbucarb; or any combination thereof.

In addition, a carbanilate herbicide may include barban; BCPC; carbasulam; carbetamide; CEPC; chlorbufam; chlorpropham; CPPC; desmedipham; phenisopham; phenmedipham; phenmedipham-ethyl; propham; swep; or any combination thereof.

In another example, a cyclohexene oxime herbicide may include alloxydim; butroxydim; clethodim; cloproxydim; cycloxydim; profoxydim; sethoxydim; tepraloxydim; tralkoxydim; or any combination thereof.

In a further example, a cyclopropylisoxazole herbicide may include isoxachlortole; isoxaflutole; or any combination thereof.

In an additional example, a dicarboximide herbicide may include benzfendizone; cinidon-ethyl; flumezin; flumiclorac; flumioxazin; flumipropyn; or any combination thereof.

Further, a dinitroaniline herbicide may include benfluralin; butralin; dinitramine; ethalfluralin; fluchloralin; isopropalin; methalpropalin; nitiralin; oryzalin; pendimethalin; prodiamine; profluralin; trifluralin; or any combination thereof.

In addition, a dinitrophenol herbicide may include dinofenate; dinoprop; dinosam; dinoseb; dinoterb; DNOC; etinofen; medinoterb; or any combination thereof.

In a further example, adiphenyl ether herbicide may include ethoxyfen. Further, a nitrophenyl ether herbicide may include acifluorfen; aclonifen; bifenox; chlomethoxyfen; chlornitrofen; etnipromid; fluorodifen; fluoroglycofen; fluoronitrofen; fomesafen; furyloxyfen; halosafen; lactofen; nitrofen; nitrofluorfen; oxyfluorfen; or any combination thereof.

In another example, a dithiocarbamate herbicide may include dazomet; metam; or any combination thereof.

In a further example, a halogenated aliphatic herbicide may include alorac; chloropon; dalapon; flupropanate; hexachloroacetone; iodomethane; methyl bromide; monochloroacetic acid; SMA; TCA; or any combination thereof.

In an additional example, a imidazolinone herbicide may include imazamethabenz; imazamox; imazapic; imazapyr; imazaquin; imazethapyr; or any combination thereof.

Further, a nitrile herbicide may include bromobonil; bromoxynil; chloroxynil; dichlobenil; iodobonil; ioxynil; pyraclonil; or any combination thereof.

In another example, an organophosphorus herbicide may include amiprofos-methyl; anilofos; bensulide; bilanafos; butamifos; 2,4-DEP; DMPA; EBEP; fosamine; glufosinate; glyphosate; piperophos; or any combination thereof.

In a further example, an oxadiazolone herbicide may include dimefuron; methazole; oxadiargyl; oxadiazon; or any combination thereof.

In an additional example, a phenoxy herbicide may include bromofenoxim; clomeprop; 2,4-DEB; 2,4-DEP; difenopenten; disul; erbon; etnipromid; fenteracol; trifopsime; or any combination thereof.

In an example, a phenoxyacetic herbicide may include 4-CPA; 2,4-D; 3,4-DA; MCPA; MCPA-thioethyl; 2,4,5-T; or any combination thereof.

In another example, a phenoxybutyric herbicide may include 4-CPB; 2,4-DB; 3,4-DB; MCPB; 2,4,5-TB; or any combination thereof.

In an additional example, a phenoxypropionic herbicide may include cloprop; 4-CPP; dichlorprop; dichlorprop-P; 3,4-DP; fenoprop; mecoprop; mecoprop-P; or any combination thereof.

In a further example, an aryloxyphenoxypropionic herbicide may include chlorazifop; clodinafop; clofop; cyhalofop; diclofop; fenoxaprop; fenoxaprop-P; fenthiaprop; fluazifop; fluazifop-P; haloxyfop; haloxyfop-P; isoxapyrifop; metamifop; propaquizafop; quizalofop; quizalofop-P; trifop; or any combination thereof.

In another example, a phenylenediamine herbicide may include dinitramine; prodiamine; or any combination thereof.

Further, a pyrazole herbicide may include azimsulfuron; difenzoquat; halosulfuron; metazachlor; pyrazosulfuron; pyroxasulfone; or any combination thereof.

In addition, a benzoylpyrazole herbicide may include benzofenap; pyrasulfotole; pyrazolynate; pyrazoxyfen; topramezone; or any combination thereof.

In another example, a phenylpyrazole herbicide may include fluazolate; nipyraclofen; pyraflufen; or any combination thereof.

In a further example, a pyridazine herbicide may include credazine; pyridafol; pyridate; or any combination thereof.

In an additional example, a pyridazinone herbicide may include brompyrazon; chloridazon; dimidazon; flufenpyr; metflurazon; norflurazon; oxapyrazon; pydanon; or any combination thereof.

Further, a pyridine herbicide may include aminopyralid; cliodinate; clopyralid; dithiopyr; fluroxypyr; haloxydine; picloram; picolinafen; pyriclor; pyroxsulam; thiazopyr; triclopyr; or any combination thereof.

In addition, a pyrimidinediamine herbicide may include iprymidam; tioclorim; or any combination thereof.

In an example, a quaternary ammonium herbicide may include cyperquat; diethamquat; difenzoquat; diquat; morfamquat; paraquat; or any combination thereof.

In another example, a thiocarbamate herbicide may include butylate; cycloate; di-allate; EPTC; esprocarb; ethiolate; isopolinate; methiobencarb; molinate; orbencarb; pebulate; prosulfocarb; pyributicarb; sulfallate; thiobencarb; tiocarbazil; tri-allate; vernolate; or any combination thereof.

In another example, a thiocarbonate herbicide may include dimexano; EXD; proxan; or any combination thereof.

Further, a thiourea herbicide may include methiuron. In addition, a triazine herbicide may include dipropetryn; triaziflam; trihydroxytriazine; or any combination thereof.

In an example, a chlorotriazine herbicide may include atrazine; chlorazine; cyanazine; cyprazine; eglinazine; ipazine; mesoprazine; procyazine; proglinazine; propazine; sebuthylazine; simazine; terbuthlylazine; trietazine; or any combination thereof.

In another example, a methoxytriazine herbicide may include atraton; methometon; prometon; secbumeton; simeton; terbumeton; or any combination thereof.

In an additional example, a methylthiotriazine herbicide may include ametryn; aziprotryne; cyanatryn; desmetryn; dimethametryn; methoprotryne; prometryn; simetryn; terbutryn; or any combination thereof.

In a further example, a triazinone herbicide may include ametridione; amibuzin; hexazinone; isomethiozin; metamitron; metribuzin; or any combination thereof.

In another example, a triazole herbicide may include amitrole; cafenstrole; epronaz; flupoxam; or any combination thereof.

In an example, a triazolone herbicide may include amicarbazone; bencarbazone; carfentrazone; flucarbazone; propoxycarbazone; sulfentrazone; thiencarbazone; or any combination thereof.

Further, a triazolopyrimidine herbicide may include cloransulam; diclosulam; florasulam; flumetsulam; metosulam; penoxsulam; pyroxsulam; or any combination thereof.

In addition, a uracil herbicide may include butafenacil; bromacil; flupropacil; isocil; lenacil; terbacil; or any combination thereof.

In another example, a urea herbicide may include benzthiazuron; cumyluron; cycluron; dichloralurea; diflufenzopyr; isonoruron; isouron; methabenzthiazuron; monisouron; noruron; or any combination thereof.

In a further example, a phenylurea herbicide may include anisuron; buturon; chlorbromuron; chloreturon; chlorotoluron; chloroxuron; daimuron; difenoxuron; dimefuron; diuron; fenuron; fluometuron; fluothiuron; isoproturon; linuron; methiuron; methyldymron; metobenzuron; metobromuron; metoxuron; monolinuron; monuron; neburon; parafluron; phenobenzuron; siduron; tetrafluron; thidiazuron; or any combination thereof.

Further, the herbicide may be a sulfonylurea herbicide. For example, a pyrimidinylsulfonylurea herbicide may include amidosulfuron; azimsulfuron; bensulfuron; chlorimuron; cyclosulfamuron; ethoxysulfuron; flazasulfuron; flucetosulfuron; flupyrsulfuron; foramsulfuron; halosulfuron; imazosulfuron; mesosulfuron; nicosulfuron; orthosulfamuron; oxasulfuron; primisulfuron; pyrazosulfuron; rimsulfuron; sulfometuron; sulfosulfuron; trifloxysulfuron; or any combination thereof. In addition, a triazinylsulfonylurea herbicide may include chlorsulfuron; cinosulfuron; ethametsulfuron; iodosulfuron; metsulfuron; prosulfuron; thifensulfuron; triasulfuron; tribenuron; triflusulfuron; tritosulfuron; or any combination thereof.

In another example, thiadiazolylurea herbicides may include buthiuron; ethidimuron; tebuthiuron; thiazafluron; thidiazuron; or any combination thereof.

In a further example, an unclassified herbicide may include acrolein; allyl alcohol; azafenidin; benazolin; bentazone; benzobicyclon; buthidazole; calcium cyanamide; cambendichlor; chlorfenac; chlorfenprop; chlorflurazole; chlorflurenol; cinmethylin; clomazone; CPMF; cresol; ortho-dichlorobenzene; dimepiperate; endothal; fluoromidine; fluridone; flurochloridone; flurtamone; fluthiacet; indanofan; methyl isothiocyanate; OCH; oxaziclomefone; pentachlorophenol; pentoxazone; phenylmercury acetate; pinoxaden; prosulfalin; pyribenzoxim; pyriftalid; quinoclamine; rhodethanil;

sulglycapin; thidiazimin; tridiphane; trimeturon; tripropindan; tritac; or any combination thereof.

In a further exemplary embodiment, the agricultural component may include an insecticide. For example, the agricultural component may include an antibiotic insecticide, a botanically-derived insecticide, a carbamate insecticide, a dinitrophenol insecticide, a formamide insecticide, a fumigant insecticide, an insect growth regulator, a nereistoxin analogue, an organochlorine insecticide, an organophosphate insecticide, an oxadiazine insecticide, a phthalimide insecticide, a pyrazole insecticide, a pyrethroid insecticide, a pyrimidinamine insecticide, a pyrrole insecticide, a tetronic acid insecticide, a thiourea insecticide, a urea insecticide, among others, or any combination thereof. For example, an antibiotic insecticide may include allosamidin; thuringiensin; spinosad; abamectin; doramectin; emamectin; eprinomectin; ivermectin; selamectin; milbemectin; milbemycin oxime; moxidectin; or any combination thereof.

In another example, a botanically-derived insecticide may include anabasine; azadirachtin; d-limonene; nicotine; pyrethrins cinerins; cinerin I; cinerin II; jasmolin I; jasmolin II; pyrethrin I; pyrethrin II; quassia; rotenone; ryania sabadilla; or any combination thereof.

In a further embodiment, the carbamate insecticide may include bendiocarb; carbaryl; benfuracarb; carbofuran; carbosulfan; decarbofuran; furathiocarb; dimetan; dimetilan; hyquinicarb; pirimicarb; alanycarb; aldicarb; aldoxycarb; butocarboxim; butoxycarboxim; methomyl; nitrilacarb; oxamyl; tazimcarb; thiocarboxime; thiodicarb; thiofanox; allyxycarb aminocarb; bufencarb; butacarb; carbanolate; cloethocarb; dicresyl; dioxacarb; EMPC; ethiofencarb; fenethacarb; fenobucarb; isoprocarb; methiocarb; metolcarb; mexacarbate; promacyl; promecarb; propoxur; trimethacarb; XMC; xylylcarb; or any combination thereof.

In an additional embodiment, the dinitrophenol insecticide may include dinex; dinoprop; dinosam; DNOC; cryolite; sodium hexafluorosilicate; sulfluramid; or any combination thereof.

In another exemplary embodiment, the formamide insecticide may include amitraz; chlordimeform; formetanate; formparanate; or any combination thereof. In an additional embodiment, the fumigant insecticide may include acrylonitrile; carbon disulfide; carbon tetrachloride; chloroform; chloropicrin; para-dichlorobenzene; 1,2-dichloropropane; ethyl formate; ethylene dibromide; ethylene dichloride; ethylene oxide, hydrogen cyanide; iodomethane; methyl bromide; methylchloroform; methylene chloride; naphthalene; phosphine; sulfuryl fluoride; tetrachloroethane; or any combination thereof.

In a further exemplary embodiment, the insect growth regulators may include bistrifluron; buprofezin; chlorfluazuron; cyromazine; diflubenzuron; flucycloxuron; flufenoxuron; hexaflumuron; lufenuron; novaluron, noviflumuron; penfluron; teflubenzuron; triflumuron; epofenonane; fenoxycarb; hydroprene; kinoprene; methoprene, pyriproxyfen; triprene; juvenile hormone I; juvenile hormone II; juvenile hormone III; chromafenozide; halofenozide; methoxyfenozide; tebutenozide; α-ecdysone; ecdysterone; diofenolan; precocene I; precocene II; precocene III; dicyclanil; or any combination thereof.

In another exemplary embodiment, the nereistoxin analogue may include bensultap; cartap; thiocyclam; thiosultap; flonicamid; clothianidin; dinotefuran; imidacloprid; thiamethoxam; nitenpyram nithiazine; acetamiprid; nitenpyram; thiacloprid; or any combination thereof.

In an additional embodiment, the organochlorine insecticide may include bromo-DDT; camphechlor; DDT; pp'-DDT; ethyl-DDD; HCH; gamma-HCH; lindane; methoxychlor; pentachlorophenol; TDE; aldrin; bromocyclen; chlorbicyclen; chlordane; chlordecone; dieldrin; dilor; endosulfan; endrin; HEOD; heptachlor; HHDN; isobenzan; isodrin; kelevan; mirex; or any combination thereof.

In a further exemplary embodiment, the organophosphate insecticide may include bromfenvinfos; chlorfenvinphos; crotoxyphos; dichlorvos; dicrotophos; dimethylvinphos; fospirate; heptenophos; methocrotophos; mevinphos; monocrotophos; naled; naftalofos; phosphamidon; propaphos; schradan; TEPP; tetrachlorvinphos; dioxabenzofos; fosmethilan; phenthoate; acethion; amiton; cadusafos; chlorethoxyfos; chlormephos; demephion; demephion-O; demephion-S; demeton; demeton-O; demeton-S; demeton-methyl; demeton-O-methyl; demeton-S-methyl; demeton-S-methylsulplhon; disulfoton; ethion; ethoprophos; IPSP; isothioate; malathionl; methacrifos; oxydemeton-methyl; oxydeprofos; oxydisulfoton; phorate; sulfotep; terbulos; thiometon; amidithion; cyanthoate; dimethoate; ethoate-methyl; formothion; mecarbam; omethoate; prothoate; sophamide; vamidothion chlorphoxim; phoxim; phoxim-methyl; azamethiphos; coumaphos; coumithoate; dioxathion; endothion; menazon; morphothion; phosalone; pyraclofos; pyridaphenthion; quinothion; dithicrofos; thicrofos; azinphos-ethyl; azinphos-methyl; dialifos; phosmet; isoxathion; zolaprofos; chlorprazophos; pyrazophos; chlorpyrifos; chlorpyrifos-methyl; butathiofos; diazinon; etrimfos; lirimfos; pirimiphos-ethyl; pirimiphos methyl; primidophos; pyrimitate; tebupirimfos; quinalphos; quinalphos-methyl; athidathion; lythidathion; methidathion; prothidathion; isazofos; triazophos; azothoate; bromophos; bromophos-ethyl; carbophenothion; chlorthiophos; cyanophos; cythioate; dicapthon; dichlofenthion; etaphos; famphur; fenchlorphos; fenitrothion; fensulfothion; fenthion; fenthion-etlhyl; heterophos; jodfenphos; mesulfenfos; parathion; parathion-methyl; phenkapton; phosnichlor; profenofos; prothiofos; sulprofos; temephos; trichlormetaphos-3; trifenofos; butonate; trichlorfon; mecarphon; fonofos; trichloronat; cyanofenphos; EPN; leptophos; crufomate; fenamiphos; fosthietan; mephosfolan; phosfolan, pirimetaphos; acephate; isocarbophos; isofenphos; methamidophos; propetamphos; dimefox; mazidox; mipafox; or any combination thereof.

In an additional embodiment, the oxadiazine insecticide may include indoxacarb. In a further embodiment, the phthalimide insecticide may include dialifos; phosmet; tetramethrin; or any combination thereof. In an example, the pyrazole insecticide may include acetoprole; ethiprole; fipronil; tebufenpyrad; tolfenpyrad; vaniliprole; or any combination thereof.

In an additional embodiment, the pyrethroid insecticide may include acrinathrin; allethrin; bioallethrin; barthrin; bifenthrin; bioethanomethrin; cyclothrin; cycloprothrin; cyfluthrin; beta-cyfluthrin; cyhalothrin; gamma-cyhalothrin; lambda-cyhalothrin; cypermethrin; alpha-cypermethrin; beta-cypermethrin; theta-cypermethrin; zeta-cypermethnn; cyphenothrin; deltamethrin; dimefluthrin; dimethrin; empenthrin; fenfluthrin; fenpirithrin; fenpropathrin; fenvalerate; esfenvalerate; flucythrinate; fluvalinate; tau-fluvalinate; furethrin; imiprothrin; metofluthrin; permethrin; biopennethrin; transpermethnn; phenothrin; prallethrin; profluthrin; pyresmethrin; resmethrin; bioresimethrin; cismethrin; tefluthrin; terallethrin; tetramethrin; tralomethrin; transfluthrin; etofenprox; flufenprox; halfenprox; protrifenbute; silafluofen; or any combination thereof. In another example, the pyrimidinamine insecticide may include flufenerim; pyrimidifen; or any combination thereof. In a further example, the pyrrole insecticides may include chlorfenapyr.

In an additional example, the tetroniic acid insecticide may include spiromesifen, the thiourea insecticide may include diafenthiuron, and the urea insecticide may include flucofuron; sulcofuron; or any combination thereof. Other insecticides may include closantel; clorpyrifos, crotamiton; EXD; fenazaflor; fenoxacrim; hydramethylnon; isoprothiolane; malonoben, metoxadiazone; nifluridde; pyridaben; pyridalyl; rafoxanide; triarathene; triazamate; or any combination thereof.

In a particular example, the insecticide may include a pyrethroid insecticide. For example, a pyrethroid type insecticide may be a cypermethrin or bifenthrin insecticide.

The agricultural composition may include the agricultural component in an amount between about 0.5% and about 95% by weight, such as greater than about 25% by weight, or at least about 27% by weight based oil the total organic composition of the agricultural composition, excluding water. For example, the agricultural composition may include at least about 35% by weight of the agricultural component, such as at least about 38% by weight, or at least about 40% by weight of the agricultural component.

The agricultural composition includes the agricultural component and a solvent composition. In an exemplary embodiment, the solvent composition includes one or more solvents. In particular, the solvent composition includes an amide solvent having a structure according to Formula I.

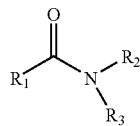

(I)

In an example, $R_1$ may be a hydrocarbon group, such as a $C_3$ to $C_{15}$ hydrocarbon group. For example, $R_1$ may be a $C_{13}$, $C_{11}$ or less hydrocarbon group. In another example, $R_1$ may include a $C_5$ to $C_{11}$ hydrocarbon group, such as a $C_7$ to $C_9$ hydrocarbon group. Alternatively, $R_1$ may be a $C_5$ to $C_{11}$ hydrocarbon group. In an embodiment, $R_1$ may include a hydrocarbon group, such as an alkyl group, an unsaturation, one or more heteroatom, an aromatic ring system, a saturated ring system, a second amide group, or any combination thereof.

In an embodiment in which the amide is formed through reaction of a fatty acid with an amine, $R_1$ may be derived from a single fatty acid or a blend of fatty acids. For example, the fatty acids may include a short or medium chain fatty acid. Embodiments include $C_4$-$C_{16}$ acids, such as $C_6$-$C_{12}$ acids, $C_6$-$C_{10}$ acids, or even $C_8$-$C_{10}$ acids, or alternatively $C_4$-$C_6$ acids, or any combinations thereof. An example of a suitable short chain fatty acid includes hexanioic, octanoic, decanoic acid, or any combination thereof. In a particular embodiment, the amide solvent is formed from a blend of fatty acids within the ranges above.

In an embodiment, $R_2$ or $R_3$ may independently include alkyl groups, amine groups, ether groups, or any combination thereof. In a particular embodiment, $R_2$ or $R_3$ may independently include an allyl group, such as a methyl, ethyl, propyl, or butyl group, or any combination thereof. In a further example, the $R_2$ or $R_3$ may form a ring incorporating the nitrogen of the amide. For example, $R_2$ and $R_3$ may act to form a morpholine group, a saturated ring, an unsaturated ring, a pyrrolidine group, or a piperidine group. In particular, $R_2$ or $R_3$ independently may be a hydrocarbon group selected from the group consisting of methyl, ethyl, propyl, butyl, and any combinations thereof. In another example, $R_2$ and $R_3$ may form a ring hydrocarbon group selected from the group consisting of —$CH_2CH_2OCH_2CH_2$—, —$CH_2CH_2CH_2CH_2$—, and —$CH_2CH_2CH_2CH_2CH_2$—.

In an exemplary embodiment, the amide solvent may be formed through reaction of a fatty acid with an amine. In a particular example, the amine is di-substituted, which may result in a liquid amide derivative. For example, the amine may include diallyl amines or ring structures, such as morpholine, dimethylamine, diethylamine, dibutylamine, diisopropylamine, pyrrolidine, piperidine, or any combination thereof. The desired amides may also be prepared from other raw materials including esters and acid halides.

In a particular embodiment, the amide solvent is a morpholine amide, such as an amide derived from a fatty acid and morpholine. For example, the morpholine amide may conform to the structure of Formula II.

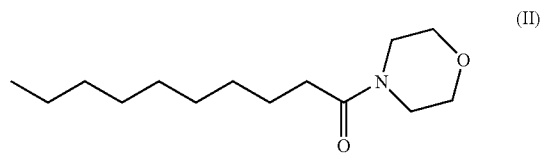

(II)

In a further example, the amide solvent may be a dialkyl amide solvent, such as a dimethylamide solvent, diethylamide solvent, dipropylamide solvent, or any combination thereof, such as illustrated in Formula III.

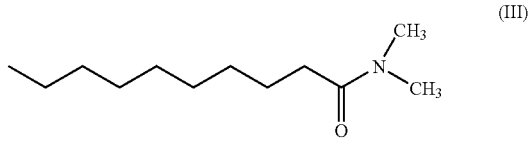

(III)

In a particular embodiment, the amide solvent has a melting point not greater than about 20° C., such as not greater than about 15° C., or even not greater than about 10° C. In an exemplary embodiment, the amide solvent has a molecular weight between about 150 and 270. In particular, the amide solvent may have a molecular weight between about 170 and 240.

In addition, the amide solvent may exhibit low water solubility and desirable solvency properties. For example, the amide solvent may be soluble in water to an amount not greater than about 2 wt %, such as not greater than about 1.5 wt %, or even not greater than about 1.0 wt %. In particular, the amide solvent may be soluble in water to an amount not greater than about 5000 ppm.

In addition, the solvent composition may include other solvents, such as alkyl benzenes, alkyl naphthalenes, methyl esters of fatty acids, aliphatic hydrocarbons, cycloaliphatic hydrocarbons, fuel oils, isophorone, methyl ethyl ketone, N-methylpyrolidone, butyl lactate, dimethyl sulfoxide, acetophenone, or any combination thereof. In general, any solvent or solvents that provide homogenous solutions when used in combination the amide solvent may be used.

In a particular embodiment, a solvent composition includes a significant amount of the amide solvent. In an example, the solvent composition may include at least about 50% by weight of the amide solvent based on the weight of the solvent composition. For example, the solvent composition may include at least about 75% of the amide solvent, such as at least about 90% by weight, or even at least about 95% by weight of the amide solvent based on the weight of the solvent composition. In a particular embodiment, the solvent composition consists essentially of the amide solvent, such as including about 100% by weight of the amide solvent based on1 the weight of the solvent composition. In a further example, the solvent composition is substantially free of water. In an exemplary embodiment, a solvent composition includes a second solvent in an amount not greater than about 75% by weight, such as an amount not greater than about 50%, not greater than about 25%, not greater than about 15%, not greater than 10% by weight, or not greater than about 5% by weight. In a particular example, the solvent composition is substantially free of a solvent other than the amide solvent. In particular, the solvent composition may be a morpholine amide solvent.

Further, the solvent composition exhibits desirable solvency relative to particular agricultural compositions or components. For example, the solvency of the agricultural component in the solvent composition may be expressed as a ratio of the highest amount of an agricultural component that dissolves to the amount of solvent composition in an agricultural composition. In a particular embodiment, the ratio may be at least about 0.5. In further example, the ratio may be at least about 0.8, such as at least about 1.0, or even at least about 1.1. In an exemplary embodiment, the ratio may be less than about 10, such as less than about 5.

In an exemplary embodiment, the agricultural composition includes not greater than about 55% by weight of the solvent composition based on the total weight of the organic components in the composition, excluding water. For example, the composition may include not greater than about 50% by weight of the solvent composition, such as not greater than about 45% by weight of the solvent composition. Further, the solvent composition may be included in the agricultural composition in an amount of at least about 5% by weight based on the total weight of the organic components in the agricultural composition, excluding water. For example, the solvent composition may be included in an amount of at least about 10% by weight, such as at least about 20% by weight, at least about 25% by weight, or even at least about 30% by weight.

In addition, the agricultural composition may include an emulsifier or an emulsifier blend. For example, the emulsifier may include an anionic calcium, sodium, or amine neutralized linear alkylsulfonate type surfactant, a phosphate ester of nonionic surfactant, cationic tallow amine surfactant, nonionic surfactant, or any combination thereof. An example of an anionic surfactant includes the alkali metal, alkaline earth or amine salt of dodecyl benzene sulphonic acid or another alkylarylsulphonic acid, sodium dialkyl sulphosuccinate, such as sodium diisoctylsulphosuccinate, an amine salt of an ether sulphate, or any combination thereof.

An example of a nonionic surfactant includes a condensation product of a fatty acid ester, a linear or branched fatty alcohol, a fatty amine with ethylene or propylene oxide, an alkyl-, alkenyl-, or polyaryl-substituted phenol with ethylene or propylene oxide, a fatty ester of a polyhydric alcohol ester (e.g., a sorbitan fatty acid ester), a condensation product of such an ester with ethylene oxide (e.g., polyoxyethylene sorbitan fatty acid ester), a block copolymer of ethylene oxide and propylene oxide, an ethoxylated lanolin alcohol, an ethoxylated lanolin acid, or any combination thereof. An example of a cationic surfactant includes, for example, an acetate or oleate of aliphatic mono-, di- or polyamines, or any combination thereof. Anionic/nionionic blends may be used.

Many suitable emulsifiers are available from Huntsman Petrochemical Corporation under the tradenames Surfonic®, Nansa®, Termul®, or any combination thereof.

In particular, the emulsifier blend may be included in an amount not greater than about 50% by weight based on the total organic composition, excluding water. For example, the emulsifier or emulsifier blend may be included in an amount not greater than about 35% by weight, such as not greater than about 20% by weight, not greater than about 15% by weight, not greater than about 10% by weight, or even as low as 5% by weight or lower based on the total composition weight, excluding water. The amount of emulsifier included in the agricultural composition is typically driven by the type of agricultural composition or the desired performance of the agricultural composition.

In an exemplary embodiment, a method for preparing an agricultural composition includes blending an amide solvent in an amount not greater than about 55% by weight of an agricultural component to form a solution. The amide solvent may have a structure according to Formula I, wherein $R_1$ comprises a $C_3$ to $C_{15}$ hydrocarbon group, and where an $R_2$ and $R_3$ comprise a C1 or higher hydrocarbon group. The method may further include blending an emulsifier with the solution. Further, other solvents or agricultural components may be blended with the solution to form the agricultural composition.

In a particular embodiment, the agricultural composition may be formed as an emulsifiable concentrate including the agricultural component, the amide solvent, and an emulsifier. In a further example, the agricultural composition may be formed as a water-based emulsion. For example, a solution including the amide solvent, an agricultural component, and emulsifiers may be blended with a portion of water. In a further exemplary embodiment, the agricultural composition may be formed as a suspo-emulsion, including suspended solids within the solution of agricultural component, amide solvent, and emulsifiers. For example, an additional agricultural component may be included in solid form within the solution to form the suspo-emulsion. Further, the agricultural composition may be formulated as a micro-emulsifiable concentrate.

Particular embodiments of the above composition exhibit advantageous technical features relative to typical agricultural compositions. For example, the agricultural composition exhibits low odor and low volatile organic carbon content (low VOC content), such as when measured by the California VOC-TGA analytical method, EPA Reference Method 24. Further, solvent compositions including the amide solvent exhibit lower toxicity and more facile bidegradation when compared to traditional solvents. Such solvent compositions exhibit low water solubility, low toxicity, low odor, higher flash point, low volatility, while simultaneously exhibiting higher solvency for particular agricultural components.

In a particular example, a morpholine derivative of a fatty acid amide exhibits desirable solvency for agricultural components such as propanil, bifenthrin, 2,4-D acid, deltamethrin, clomazone, or any combination thereof.

EXAMPLES

Example 1

An amide solvent is formed from "C-810" fatty acid, which is a light cut fatty acid commercially available from Proctor & Gamble. "C-810" includes 3-5 wt. % $C_6$ fatty acid, 53-60 wt. % $C_8$ fatty acid, 34-42 wt. % $C_{10}$ fatty acid, and 0-2 wt. % $C_{12}$ fatty acid. The "C-810" is reacted with morpholine to form the amide solvent, referred to herein as "C-810 morpholine amide solvent."

Morpholine (552 g, 6.35 moles) and "C810" (978 g, 6.35 moles) are placed in a 3-liter glass reactor equipped with an overhead stirrer and a Dean-Stark trap for removing water. The mixture is heated to 150° C. and is stirred for 6 hours, during which time the reaction bi-product (water) is continuously removed by means of the Dean-Stark trap. After water ceases to be collected, an additional amount of morpholine is added to the reactor (approximately 52 g, 0.6 moles). The temperature is held at 150° C. for 2 additional hours with stirring. The temperature is raised to 170° C. and the remaining morpholine, if any, is removed by passing a gentle stream of nitrogen through the reactor for a period of 2 hours before cooling to ambient temperature.

Example 2

The C-810 morpholine amide solvent is mixed with the following components to form a herbicide emulsifiable concentrate (propanil EC): propanil, technical 45 wt. %; morpholine amide 43 wt. %; and emulsifier blend 12 wt. %.

Example 3

A series of experiments are performed to determine an amount of an agricultural component to be included in an emulsifiable concentrate without recrystallization of the agricultural component. Table 1 illustrates the highest test amount of agricultural component that dissolves in the solvent composition at approximately 25° C. The amount that dissolves is determined through blending an amount of the agricultural component with the solvent composition and an emulsifier blend, and storing the resulting solution at 0° C. for 2 weeks. If no crystal growth is observed, the amount is determined to have dissolved.

Table 1 illustrates the parts agricultural component, the pairs solvent composition, and the ratio of the parts agricultural component to the parts solvent composition. In this example, the solvent composition is the C-810 morpholine amide solvent.

TABLE 1

Solvency of Agricultural Component (AC)

| Agricultural Component | Agricultural Component (parts) | Solvent Composition (parts) | Ratio (AC:solvent) |
|---|---|---|---|
| Propanil | 45 | 40 | 1.12 |
| Chlorsulfuron | 1 | 89 | 0.01 |
| Cypermethrin | 44 | 44 | 1.0 |
| Bifenthrin | 25 | 67 | 0.37 |
| 2,4-D acid | 40 | 48 | 0.83 |
| 1:1 Phenmediphan/Desmediphan | 20 | 70 | 0.28 |
| Clomazone | 45 | 45 | 1.0 |
| Triclopyr | 4 | 86 | 0.04 |
| Alachlor | 50 | 50 | 1.0 |

Example agricultural compositions are formed based on the highest tested amount of agricultural component to dissolve in the solvent composition as determined above. Such example agricultural compositions are provided in Tables 2-9. Amounts are expressed in weight percent.

TABLE 2

Propanil EC

| | |
|---|---|
| Propanil, technical | 45% |
| C-810 morpholine amide solvent | 40% |
| Emulsifier blend | 15% |

TABLE 3

Chlorosurfuron EC

| | |
|---|---|
| Chlorsulfuron, technical | 1% |
| C-810 morpholine amide solvent | 89% |
| Emulsifier blend | 10% |

TABLE 4

Cypermethrin EC

| | |
|---|---|
| Cypermethrin, technical | 44% |
| C-810 morpholine amide solvent | 44% |
| Emulsifier blend | 12% |

TABLE 5

Bifenthrin EC

| | |
|---|---|
| Bifenthrin, technical | 25% |
| C-810 morpholine amide solvent | 67% |
| Emulsifier blend | 8% |

TABLE 6

2,4-D acid EC

| | |
|---|---|
| 2,4-D acid, technical | 40% |
| C-810 morpholine amide solvent | 48% |
| Emulsifier blend | 12% |

TABLE 7

Phenmediphan & Desmediphan EC

| | |
|---|---|
| Phenmediphan | 10% |
| Desmediphan | 10% |
| C-810 morpholine amide solvent | 70% |
| Emulsifier blend | 10% |

TABLE 8

Clomazone EC

| | |
|---|---|
| Clomazone, technical | 45% |
| C-810 morpholine amide solvent | 45% |
| Emulsifier blend | 10% |

TABLE 9

Triclopyr EC

| | |
|---|---|
| Triclopyr, technical | 4% |
| C-810 morpholine amide solvent | 86% |
| Emulsifier blend | 10% |

TABLE 10

Fluoxastrobin EC

| | |
|---|---|
| Fluoxastrobin | 3% |
| C-810 morpholine amide solvent | 89% |
| Emulsifier blend | 8% |

TABLE 11

Alachlor EC

| | |
|---|---|
| Alochlor | 45% |
| C-810 morpholine amide solvent | 45% |
| Emulsifier blend | 10% |

TABLE 12

Cypermethrin EC

| | |
|---|---|
| Cypermethrin | 44% |
| C-810 morpholine amide solvent | 22% |
| Aromatic 150 (Exxon Mobil) | 22% |
| Emulsifier blend | 12% |

TABLE 13

Propanil EC

| | |
|---|---|
| Propanil | 40% |
| C-810 morpholine amide solvent | 30% |
| Propylene carbonate (Huntsman) | 15% |
| Emulsifier blend | 15% |

Example 5

The C-810 morpholine amide solvent is tested to determine water solubility. The water solubility is compared with solubility data available for a dimethyamide.

TABLE 13

Water Solubility

| Solvent | Solubility in Water (wt %) |
|---|---|
| C-810 morpholine amide solvent | <1% |
| N,N-dimethyldecanamide | 3.8% |

The above-disclosed subject matter is to be considered illustrative, and not restrictive, and the appended claims are intended to cover all such modifications, enhancements, and other embodiments, which fall within the true scope of the present invention, Thus, to the maximum extent allowed by law, the scope of the present invention is to be determined by the broadest permissible interpretation of the following claims and their equivalents, and shall not be restricted or limited by the foregoing detailed description.

The invention claimed is:

1. A composition comprising:
   a non-triazole functional pesticide; and
   a solvent composition in an amount not greater than about 55% by weight, the solvent composition including an amide having a structure of

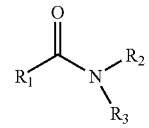

wherein $R_1$ is a $C_3$ to $C_{15}$ hydrocarbon group selected from the group consisting of —$CH_2CH_2OCH_2CH_2$—, —$CH_2CH_2CH_2CH_2$—, and —$CH_2CH_2CH_2CH_2CH_2$—, and wherein $R_2$ and $R_3$ form a ring hydrocarbon group.

2. The composition of claim 1, wherein $R_1$ comprises an alkyl group.

3. The composition of claim 1, wherein $R_2$ and $R_3$ form a morpholine group, a saturated ring, an unsaturated ring, a pyrrolidine group, or a piperidine group.

4. The composition of claim 1, wherein the amide is derived from $C_4$-$C_{16}$ fatty acids.

5. The composition of claim 1, wherein the amide comprises a morpholine amide.

6. The composition of claim 1, wherein the amount of solvent composition is not greater than about 50% by weight of the composition.

7. The composition of claim 1, wherein a ratio of the amount of the non-triazole functional pesticide to the amount of the solvent composition is at least about 0.5.

8. The composition of claim 7, wherein the ratio is at least 0.8.

9. The composition of claim 1, wherein the solvent composition includes at least 50% by weight of the amide based on the weight of the solvent composition.

10. The composition of claim 1, wherein the solvent composition is substantially free of water.

11. The composition of claim 1, wherein the amide has a water solubility not greater than about 2.0 wt %.

12. The composition of claim 1, comprising greater than about 25% by weight of the non-triazole functional pesticide.

13. The composition of claim 1, wherein the non-triazole functional pesticide is an amide or anilide type herbicide.

14. The composition of claim 1, wherein the non-triazole functional pesticide comprises a pyrethroid type insecticide.

15. The composition of claim 1, wherein the non-triazole functional pesticide is included in the amount of at least 27% by weight.

16. The composition of claim 1, wherein the solvent composition is included in an amount of at least 10% by weight.

17. A method of preparing an agricultural composition, the method comprising:
   blending an amide solvent in an amount not greater than about 55% by weight with an agricultural component in an amount of at least 27% by weight to form a solution, the amide solvent having a structure of

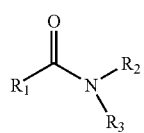
wherein $R_1$ is a $C_3$ to $C_{15}$ hydrocarbon group selected from the group consisting of —$CH_2CH_2OCH_2CH_2$—, —$CH_2CH_2CH_2CH_2$—, and —$CH_2CH_2CH_2CH_2CH_2$—, and wherein $R_2$ and $R_3$ form a ring hydrocarbon group; and
blending an emulsifier with the solution.
18. The method of claim 17, wherein the amide solvent is a morpholine amide solvent.
* * * * *

UNITED STATES PATENT AND TRADEMARK OFFICE
CERTIFICATE OF CORRECTION

PATENT NO.         : 8,298,992 B2                                   Page 1 of 1
APPLICATION NO.    : 12/300482
DATED              : October 30, 2012
INVENTOR(S)        : Stern et al.

It is certified that error appears in the above-identified patent and that said Letters Patent is hereby corrected as shown below:

In the Claims:

Column 18, Claim 1, Lines 17-20, delete "selected from the group consisting of $-CH_2CH_2OCH_2CH_2-$, $-CH_2CH_2CH_2CH_2-$, and $-CH_2CH_2CH_2CH_2CH_2$" and insert -- selected from the group consisting of $-CH_2CH_2OCH_2CH_2-$, $-CH_2CH_2CH_2CH_2-$, and $-CH_2CH_2CH_2CH_2CH_2-$ -- after "ring hydrocarbon group" therefor;

Columns 19, Lines 9-10, Column 20, Lines 1-2, Claim 17, delete "selected from the group consisting of $-CH_2CH_2OCH_2CH_2-$, $-CH_2CH_2CH_2CH_2-$, and $-CH_2CH_2CH_2CH_2CH_2$" and insert -- selected from the group consisting of $-CH_2CH_2OCH_2CH_2-$, $-CH_2CH_2CH_2CH_2-$, and $-CH_2CH_2CH_2CH_2CH_2-$ -- after "ring hydrocarbon group" therefor.

Signed and Sealed this
Twenty-second Day of October, 2013

Teresa Stanek Rea
*Deputy Director of the United States Patent and Trademark Office*